United States Patent [19]
Dawson et al.

[11] Patent Number: 6,087,372
[45] Date of Patent: Jul. 11, 2000

[54] METHOD OF ENHANCING COGNITION WITH 2-(4-METHOXYPHENYL)-PYRAZOLO[4,3-C]QUINOLIN-3-ONE

[75] Inventors: Gerard Raphael Dawson, Saffron Walden; Angus Murray MacLeod, Bishops Stortford; Guy Ralph Seabrook, London, all of United Kingdom

[73] Assignee: Merck Sharp & Dohme Ltd., Hoddesdon, United Kingdom

[21] Appl. No.: 09/308,821

[22] PCT Filed: Nov. 26, 1997

[86] PCT No.: PCT/GB97/03232

§ 371 Date: May 25, 1999

§ 102(e) Date: May 25, 1999

[87] PCT Pub. No.: WO98/24435

PCT Pub. Date: Jun. 11, 1998

[30] Foreign Application Priority Data

Dec. 6, 1996 [GB] United Kingdom .................... 9625398

[51] Int. Cl.⁷ .................................................... A01N 43/42
[52] U.S. Cl. ............................................ 514/293; 514/879
[58] Field of Search ........................................ 514/293, 879

[56] References Cited

U.S. PATENT DOCUMENTS

| | | | |
|---|---|---|---|
| 4,312,870 | 1/1982 | Yokoyama | 424/258 |
| 4,595,684 | 6/1986 | Bennett | 514/221 |
| 4,740,512 | 4/1988 | Yokoyama | 514/293 |
| 5,484,793 | 1/1996 | Dood et al. | 514/300 |

FOREIGN PATENT DOCUMENTS

| | | |
|---|---|---|
| 0 022 078 | 7/1981 | European Pat. Off. |
| WO 92/21680 | 10/1992 | WIPO |

OTHER PUBLICATIONS

International Search Report —Mar. 6, 1998.
Bennett, D. A., "Pharmacology of the Pyrazolo–Type Compounds: Agonist, Antagonist and Inverse Agonist Actions," Physiology & Behavior, vol. 41, (1987), pp. 241–245.

*Primary Examiner*—Frederick Krass
*Assistant Examiner*—Donna Jagoe
*Attorney, Agent, or Firm*—Shu M. Lee; David L. Rose

[57] ABSTRACT

The present invention provides the use of 2-(4-methoxyphenyl)-pyrazolo[4,3-c]quiniolin-3-one or a pharmaceutically acceptable salt thereof for the manufacture of a medicament for enhancing cognition, particularly in Alzheimer's Disease, a method of enhancing cognition and pharmaceutically acceptable salts such as the hemi camphor sulfonate.

2 Claims, No Drawings

METHOD OF ENHANCING COGNITION WITH 2-(4-METHOXYPHENYL)-PYRAZOLO [4,3-C]QUINOLIN-3-ONE

This application is a 371 of PCT/GB97/03232 filed Nov. 26, 1997.

The present invention provides a method of treatment for enhancing cognition (for example in the treatment of dementing illnesses such as Alzheimer's disease), the manufacture of medicaments useful for such treatment, pharmaceutical compositions and compounds.

A number of dementing illnesses and cognition deficit states are characterised by poor and often a progressive deterioration in the cognition of the sufferer. It would clearly be desirable to enhance cognition in subjects desirous of such treatments. International Patent Application No. PCT/GB 96/00377 discloses that certain $GABA\alpha_5$ receptor inverse agonists ("$\alpha 5$ inverse agonists") may be used to enhance cognition without producing convulsions. Also by choosing an as inverse agonist that does not have significant ($\alpha_1$, $\alpha_2$, or $\alpha_3$ agonism it is possible to avoid benzodiazepine receptor activity such as that associated with marked anxiolytic, sedative or anti-depressive effects.

U.S. Pat. No. 4,312,870 ("the U.S. Patent") disclosed broad groups of 2-aryl-pyrazolo[4,3-c]quinolin-3-(1 and 3H)-ones which were said to be useful in the treatment of anxiety and depression. Certain of the compounds disclosed in the U.S. Patent have been tested further, see for example Yokoyama et al., J. Med. Chem., 1982, 25, 337–339 and Bennett, Physiology & Behaviours, 1987, 41, 241–245. The Yokoyama paper disclosed that the compounds of the formula (I):

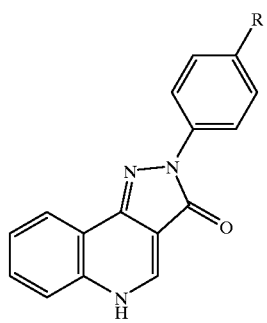

Ia, R = H
Ib, R = Cl
Ic, R = $OCH_3$ wherein R is (a) hydrogen, (b) chlorine or (c) methoxy have an order of magnitude greater affinity for the benzodiazepine receptors than diazepam with 3a being a potent benzodiazepine antagonist, 3b being diazepam-like and 3c acting as an agonist (diazepam-like) at lower doses and antagonist at higher doses. The latter, more detailed paper by Bennett concludes that compounds Ib offers the potential for effective anxiolytic therapy (having been employed clinically) and that compound Ia could be used for the treatment of benzodiazepine overdose. Compound Ic was shown to be only half as effective as related compounds in producing anti-conflict effects.

Subsequently the skilled worker is aware that none of the compounds of formula I proved to be acceptable as marketed medicaments (from which the skilled worker could conclude that the compounds of formula Ia and Ib cause unacceptable side effects or lack of clinical efficacy). Finally, the assignee of the U.S. Patent demonstrated the lack of value attributed to the compounds by them by not paying the patent renewal fees on the UK equivalent of the U.S. Patent by 1994.

Clearly, in view of what the skilled worker knows about the compounds of the U.S. Patent, the skilled worker would not investigate their behaviours further. However, most surprisingly, it has been found that 2-(4-methoxyphenyl)-pyrazolo[4,3-c]quinolin-3(5H)-one and its pharmaceutically acceptable salts are useful for the treatment of conditions requiring the enhancement of cognition such as those indicated hereinbefore.

Accordingly, the present invention provides a method of treatment of a condition requiring the enhancement of cognition in a subject which comprises administering to the subject in need thereof a cognition enhancing amount of 2-(4-methoxyphenyl)-pyrazolo[4,3-c]quinolin-3(5H)-one or a pharmaceutically acceptable salt thereof.

The method will be applied to a mammal, most aptly to a human, preferably to a human suffering from a dementing illness and most preferably to a human suffering from Alzheimer's disease.

It is a great advantage that the method of this invention leads to the enhancement of cognition without being convulsant. Other advantages include not being sedative. In addition, anxiolytic and anti-depressive effects are not prominent. It is believed that 2-(4-methoxyphenyl)-pyrazolo [4,3-c]quinolin-3(5H)-one and its pharmaceutically acceptable salts are able to achieve this desirable end by virtue of being a $GABA_A\alpha_5$ inverse agonist without possessing major agonist or inverse agonist properties at the $GABA_A\alpha_1$, $\alpha_2$, or $\alpha_3$ receptors.

It is considered more desirable to use a pharmaceutically acceptable salt of 2-(4-methoxyphenyl)-pyrazolo[4,3-c] quinolin-3(5H)-one. Most aptly such a salt is one which is significantly more soluble than the parent quinolinone.

Suitable pharmaceutically acceptable salts include acid addition salts with mineral or organic acids such as the salts with hydrochloric, sulphuric, hydrobromic, phosphoric, methane sulfonic, ethane sulfonic, camphor sulfonic, acetic, lactic, citric, tartaric, maleic, benzoic, propionic, succinic, fumaric, gluconic or malic acid.

Favoured salts include those of non-volatile acids. Particularly favoured salts include hemi camphor sulfonate (hemi campsylate).

The compositions are most aptly adapted for oral administration to humans although parenteral modes of administration are also envisaged, for example by intravenous, intramuscular or subcutaneous administration or topically or rectally.

For oral use of the cognition enhancer the selected compound may be administered for example in the form of a tablet or a pharmaceutically acceptable carriers or diluents, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

For oral use the cognition enhancer may be administered, for example, in the form of tablets or capsules, or as an aqueous solution or suspension. In the case of tablets for oral use, carriers which are commonly used include lactose, microcrystalline cellulose, carboxymethyl cellulose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, the cognition enhancer may be formulated as, for example, a suspension, lotion, cream or ointment employing a pharmaceutically acceptable carrier such as, for example, water, mixtures of water and water-miscible solvents such as lower alkanes, vegetable oils, polyalkylene glycols and the like.

The pharmaceutical preparation may also contain non-toxic auxiliary substances such as emulsifying, preserving, wetting agents, bodying agents and the like, as for example, polyethylene glycois 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

When a cognition enhancer is used in a human subject, the daily dosage will normally be determined by the prescribing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, dosage outside these limits may be used. Generally the daily dose will be administered as in from 1 to 6 times a day, generally 1 to 3 times per day.

Generally unit dose forms for oral administration will contain from 1 to 800 mgs, more usually 2.5 to 250 mgs, preferably 5 to 100 mgs, for example 10, 20 or 50 mgs. Preferably the unit dosage form is in the form of a tablet.

This invention also provides a method of manufacture of a medicament for the enhancement of cognition, which comprises the use of 2-(4-methoxyphenyl)-pyrazolo[4,3-c] quinolin-3-one or a pharmaceutically acceptable salt thereof.

In a further aspect this invention provides a pharmaceutically acceptable salt of 2-(4-methoxyphenyl)-pyrazolo[4,3-c]quinolin-3(5H)-one and a pharmaceutically acceptable carrier therefor.

In another aspect this invention provides a pharmaceutical composition which comprises a cognition enhancing non-anxiolytic amount of 2-(4-methoxyphenyl)-pyrazolo [4,3-c] quinolin-3(5H)-one or a pharmaceutically acceptable salt thereof and a pharmaceutically acceptable carrier therefor.

Since said quinolinone is much more effective as an inverse agonist at $GABA_A\alpha_5$ than as an agonist at $GABA_A\alpha_1$, $\alpha_2$ or $\alpha_3$ (e.g. >−20% as compared to about +5%) the dose required for cognition enhancement is readily differentiated from the higher dose required before anxiolytic or anti-depressant behaviour (if any) can take place.

The salts of 2-(4-methoxyphenyl)-pyrazolo[4,3-c] quinolin- 3(5H)-one may be made by treatment with the required acid, for example in ethanolic solution.

Favourably the salt is in isolated form and more favourably substantially pure. Preferably the salt is crystalline.

DESCRIPTION 2-(4-Methoxvyphenyl)-2,5-dihydro-oyrazolo[4,3-c] quinolin-3-one

A mixture of ethyl 4-chloro-quinoline-3-carboxylate (10.18 g, 0.043 mol), 4-methoxyphenylhydrazine hydrochloride (8.45 g, 0.048 mol) and N-ethyldiisopropylamine (16.6 ml, 0.096 mol) in xylene (250 ml) was deoxygenated, using nitrogen, for 15 minutes. The mixture was heated at reflux, with stirring under nitrogen, for 2 hours, cooled, diluted with diethyl ether (100 ml) and treated with water (100 ml). After stirring for 30 minutes the mixture was filtered and the solid washed with diethyl ether (200 ml) then stirred in water (250 ml) at 70° C. for 30 minutes. The solid was collected by filtration then dried in vacuo to give the title compound free base as a yellow solid (12.1 g, 96%), mp 273–274° C. (propan-2-ol), MS, ES$^+$, m/z=292 for (M+H)$^+$, δ (500 MHz,DMSO-d6) 3.78 (3H,s), 7.02 (2H,d,J=9 Hz), 7.54 (1H,dd,J$_1$=J$_2$=8 Hz), 7.66 (1H,dd,J$_1$=J$_2$=8 Hz) 8.09 (2H,d,J=9 Hz), 8.21(1H,d,J=8 Hz), 8.69(1H,5), 12.76 (1H, broad res.).

EXAMPLE 1

2-(4-methoxyphenyl)-2,5-dihydro-pyrazolo[4,3-c]quinolin-3-one hemi-campsylate

The free base of Description 1 (200 mg, 0.687 mmol) in ethanol/acetone (8 ml, 1:1) at reflux was filtered and treated with a solution of (1S)-(+)-10-camphorsulphonic acid (160 mg, 0.687 mmol) in ethanol (2 ml). The mixture was allowed to cool to room temperature, aged for 1 hour, then the title compound collected by filtration as a yellow solid (205 mg), mp 240°–241° C.

EXAMPLE 2

A sulphate salt was prepared exactly as described in Example 1 by replacing the camphorsulphonic acid by sulphuric acid (0.687 mmol) m.pt 264–7° C.

EXAMPLE 3

A scored tablet may be prepared comprising:

| | |
|---|---|
| 1. Compound of Ex. 1 | 20 mg |
| 2. Lactose | 120 mg |
| 3. Microcrystalline cellulose | 40 mg |
| 4. Polyvinylpyrrolidone | 5 mg |
| 5. Magnesium sterate | 5 mg |

What is claimed is:

1. A method of treatment of a condition requiring the enhancement of cognition in a subject suffering from deterioration in the cognition of the sufferer which comprises administering to the subject in need thereof a cognition enhancing and non-convulsion-inducing amount of 2-(4-methoxyphenyl)-pyrazolo[4,3-c]quinolin-3-one or a pharmaceutically acceptable salt thereof.

2. The method of claim 1 wherein the condition requiring enhancement of cognition is Alzheimer's disease.

* * * * *